United States Patent [19]

Cortes et al.

[11] Patent Number: 5,139,681
[45] Date of Patent: Aug. 18, 1992

[54] ON-LINE MULTIDIMENSIONAL CHROMATOGRAPHIC SYSTEM WITH LARGE VOLUME INJECTION HANDLING FOR SUPERCRITICAL FLUID CHROMATOGRAPHY

[75] Inventors: Hernan J. Cortes; Robert M. Campbell, both of Midland; R. Paul Himes, Breckenbridge; Curtis D. Pfeiffer, Midland, all of Mich.

[73] Assignee: The Dow Chemical Company, Midland, Mich.

[21] Appl. No.: 594,403

[22] Filed: Oct. 9, 1990

[51] Int. Cl.$^5$ ............................................. B01D 15/08
[52] U.S. Cl. .................................. 210/659; 210/198.2; 55/386
[58] Field of Search ............ 210/635, 656, 659, 198.2; 55/67, 386; 436/161; 422/70; 73/61.1 C

[56] References Cited

U.S. PATENT DOCUMENTS

| | | | |
|---|---|---|---|
| 3,686,117 | 8/1972 | Lauer | 210/659 |
| 4,478,720 | 10/1984 | Perrut | 210/659 |
| 4,479,380 | 10/1984 | Novotony | 73/61.1 C |
| 4,500,432 | 2/1985 | Poole | 210/659 |
| 4,597,943 | 7/1986 | Sugiyama | 422/70 |
| 4,775,476 | 10/1988 | Melcher | 210/198.2 |
| 4,793,920 | 12/1988 | Cortes | 210/198.2 |
| 4,806,250 | 2/1989 | Takata | 210/659 |
| 4,913,821 | 4/1990 | Melcher | 210/198.2 |
| 4,935,145 | 6/1990 | Cortes | 210/656 |

OTHER PUBLICATIONS

Snyder, "Introduction to Modern Liquid Chromatography", John Wiley & Sons, 1979, pp. 730-731.
Campbell, "Supercritical Fluid Extraction" Journal of Microcolumn Separations vol. I No. 6 (1989) pp. 302-308.
Wright, B. W. et al., Anal. Chem. 1987, 59, pp. 38-44, Analytical Supercritical Fluid Extraction of Adsorbent Materials.
Anderson, M. R. et al., Chromatogr. Sci., 1989, 27, pp. 371-377, Supercritical Fluid Extraction as a Sample Introduction Method for Chromatography.
Hawthorne, S. B. et al., Chromatogr. Sci., 1990, 28, pp. 2-8, Quantitative Analysis Using Directly Coupled Supercritical Fluid Extraction-Capillary Gas Chromatography (SFE-GC) With a Conventional Split/Splitless Injection Port.
McNally, M. E. P. et al., J. Chromatogr., 1988, 435, pp. 63-71, Supercritical Fluid Extraction Coupled with Supercritical Fluid Chromatography for the Separation of Sulfonylurea Herbicides and Their Metabolites from Complex Matrices.
Xie, Q. L. et al., J. Chromatogr., 1989, 27, pp. 365-370, Supercritical Fluid Extraction-Supercritical Fluid Chromatography with Fraction Collection for Sensitive Analytes.
Hirata, Y. et al., Microcolumn Sep., 1989, 1, pp. 46-50, Supercritical Fluid Extraction Combined with Microcolumn Liquid Chromatography for the Analysis of Polymer Additives.
Unger, K. K. et al., Chromatogr., 1983, 282, pp.
(List continued on next page.)

*Primary Examiner*—Ernest G. Therkorn

[57] ABSTRACT

An on-line multidimensional chromatographic system and method which couples a liquid chromatograph to a supercritical fluid chromatograph. The system includes an inlet column for depositing a fraction of interest eluting from the liquid chromatograph, an interface interposed between the inlet column and the supercritical fluid chromatograph for receiving and trapping an analyte from the deposited fraction on an impactor surface, and a valve arrangement for controlling fluid flow throughout the system. After the fraction of interest has been deposited in the inlet column, the liquid chromatograph solvent is removed from the inlet column, and then the deposited fraction is extracted from the inlet column in a supercritical fluid stream. The supercritical fluid stream is directed into the interface, where the analyte is trapped while the supercritical fluid is decompressed and vented. A subsequent supercritical fluid stream is then used to introduce the trapped analyte directly into the analytical column of the supercritical fluid chromatograph.

7 Claims, 3 Drawing Sheets

OTHER PUBLICATIONS 519-526, On-Line High-Pressure Extraction-High-Performance Liquid Chromatography.

Nair, J. B. et al., LC-GC, 1988, 6, pp. 1071-1073, On-Line Supercritical Sample-Preparation Accessory for Chromatography.

Cortes, H. J. et al., Chromatogr., 1985, 349, pp. 55-61, Determination of Trace Chlorinated Benzenes in Fuel Oil by On-Line Multidimensional Chromatography Using Packed-Capillary Liquid Chromatography and Capillary Gas Chromatography.

Duquet, D. et al., HRC&CC, 1988, 11, pp. 824-829, Coupling Miniaturized Liquid Chromatography to Capillary Gas Chromatography (Micro-LC-CGC): Possibilities of Reversed Phase LC.

Cortes, H. J. et al., Anal. Chem., 1989, 61, pp. 961-965, Multidimensional Chromatography Using On-Line Microcolumn Liquid Chromatography and Pyrolysis Gas Chromatography for Polymer Characterization.

Cortes, H. J. et al., HRC&CC, 1987, 10, pp. 446-448, Porous Ceramic Bed Supports for Fused Silica Packed Capillary Columns Used in Liquid Chromatography.

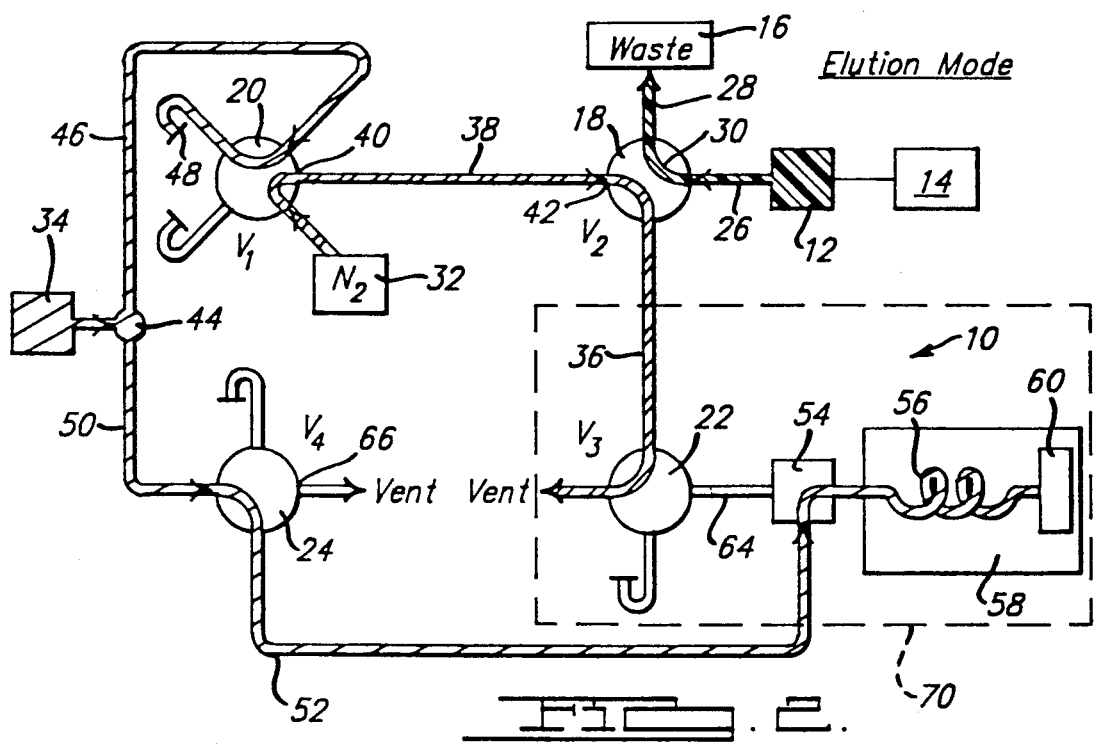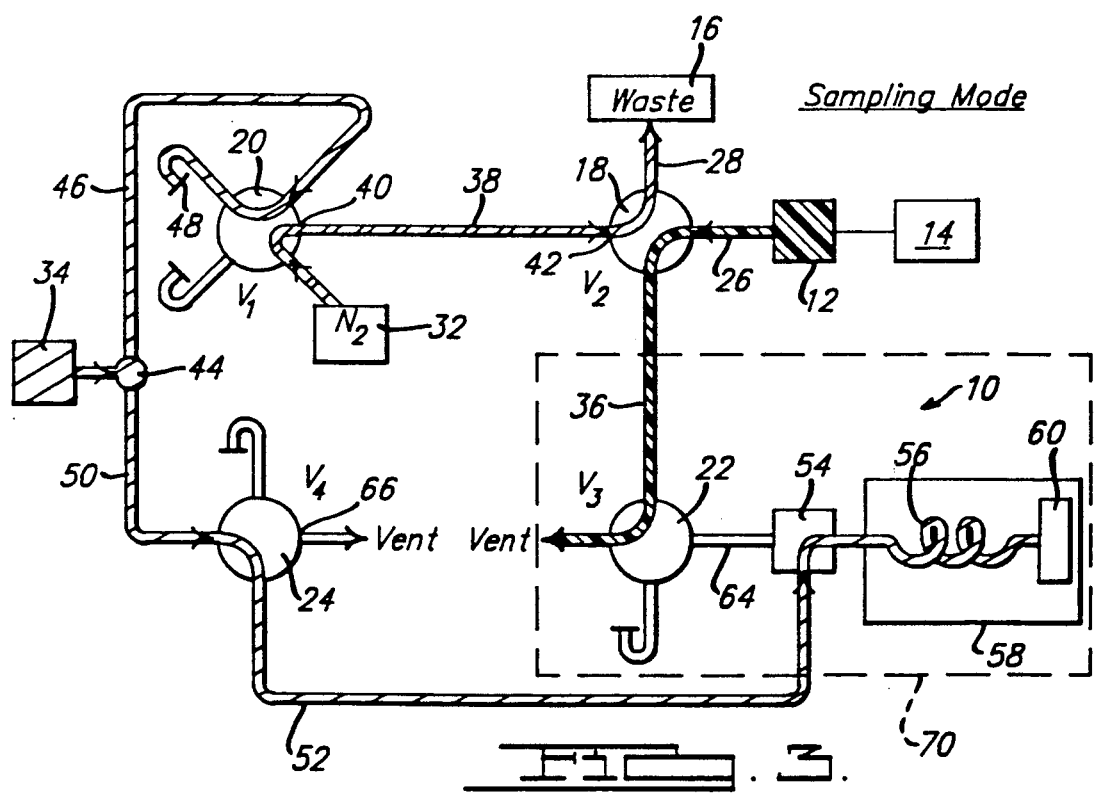

ON-LINE MULTIDIMENSIONAL CHROMATOGRAPHIC SYSTEM WITH LARGE VOLUME INJECTION HANDLING FOR SUPERCRITICAL FLUID CHROMATOGRAPHY

BACKGROUND OF THE INVENTION

The present invention relates generally to multidimensional chromatography, and in particular to an on-line system and method which couples liquid chromatography to supercritical fluid chromatography in a way that includes large injection volume fluid handling for the supercritical fluid chromatography.

The analysis of complex matrices, such as polymer additives, usually requires manual clean-up steps to remove undesirable components prior to analysis. In this regard, multidimensional chromatography offers the potential of rapidly accomplishing the necessary sample preparation or clean-up steps without manual intervention. In multidimensional chromatography, two or more separation techniques work in tandem, such that an initial separation step is followed by a further separation technique on a particular section or fraction of interest produced by the prior separation step. For example, one liquid chromatograph ("LC") could be coupled to another LC to provide multidimensional separation. Similarly, a liquid chromatograph ("LC") could be coupled to a gas chromatograph ("GC") to provide another form of multidimensional separation. However, LC-LC multidimensional chromatography can be limited in terms of sensitivity and by solvent incompatibilities. Additionally, while LC-GC multidimensional chromatography can be used successfully for analytes transportable in the gaseous mobile phase, there are quite a number of compounds which are not sufficiently volatile to be analyzed by GC.

In contrast, supercritical fluid chromatography ("SFC") enables compounds to be analyzed which are not sufficiently volatile to otherwise be analyzed by GC, such as materials having relatively high molecular weights. SFC also has the capability of utilizing a flame ionization detector ("FID") for permitting sensitive and universal detection. Thus, the creation of an LC-SFC multidimensional chromatographic system offers the potential of providing highly sensitive analysis of non-volatile compounds. However, in SFC, capillary columns (e.g., 50 µm i.d.) are typically required to obtain adequate performance. As a result of the need to use such small diameter columns for separation, the injection volumes must also be very small. In this regard, the injection volumes are generally limited to a range from less than one nanoliter to just a few nanoliters. This limitation represents a substantial impediment to the development of an effective "on-line" LC-SFC coupled system, because relatively large solvent volumes are typically used in LC to provide the necessary separation. In this context, the term "on-line" refers to a multidimensional system which provides fluid communication between the system components so that the analytical process may be conducted on a continuous basis without resort to manual collection steps.

Accordingly, it is a principal objective of the present invention to provide an on-line LC-SFC multidimensional chromatographic system and method which permits large solvent volumes to be employed for purposes of LC separation, without requiring the actual introduction of large fluid volumes into the supercritical fluid chromatograph.

It is another objective of the present invention to provide an on-line LC-SFC multidimensional chromatographic system and method which first removes the LC solvent and then traps the analyte before the analyte is introduced into the supercritical fluid chromatograph.

It is a further objective of the present invention to provide an interface for the system which is capable of trapping the analyte in a confined region in order to minimize band broadening of the chromatographic peaks in the subsequent SFC step.

SUMMARY OF THE INVENTION

To achieve the forgoing objectives, the present invention provides an on-line LC-SFC multidimensional chromatographic system which includes an inlet column for depositing a fraction of interest eluting from a liquid chromatograph, a pump for causing a supercritical fluid to extract the deposited fraction as an analyte, an interface interposed between the inlet column and a supercritical fluid chromatograph for trapping the analyte before introducing the analyte into the supercritical fluid chromatograph, and a valve arrangement for controlling fluid flow throughout the system. In accordance with the method of the present invention, the liquid chromatograph is used to separate and detect a fraction of interest from a sample material injected into the solvent stream of the liquid chromatograph. Once the fraction of interest is detected, the fluid flow eluting from the liquid chromatograph is directed into and through the inlet column, so that at least a portion of the fraction is deposited on an interior surface of the inlet column. Solvent is then removed from the inlet column by causing an inert gas stream to pass through the inlet column. The deposited fraction or analyte is then extracted from the inlet column and conveyed to the interface by a supercritical fluid stream. The interface traps the analyte in a confined area while decompressing the supercritical fluid into a gas and venting the decompressed supercritical fluid from the interface. A subsequent supercritical fluid stream is then used to remove the trapped analyte from the interface and introduce the analyte into the supercritical fluid chromatograph.

Accordingly, it should be appreciated that the system and method of the present invention permits a large volume of solvent to be used for the LC separation step, as the inlet column and valve arrangement enables the solvent to be removed from the system before the SFC step takes place. Additionally, the interface of the present invention permits the supercritical fluid used for extracting the deposited analyte from the inlet column to also be removed from the system by trapping the analyte onto a predetermined surface and venting this supercritical fluid from the system. Thus, the volume of supercritical fluid required to ultimately introduce the trapped analytes into the supercritical fluid chromatograph is quite small.

The interface includes a restricted diameter passage for receiving the supercritical fluid stream conveying the analyte from the inlet column, a transfer passage for permitting the supercritical fluid to decompress and be vented from the system, and an impactor located at the junction of the restricted diameter passage and the transfer passage to provide a predetermined surface for trapping the analyte as the supercritical fluid decompresses. The interface also includes an output passage associated with the impactor for enabling the trapped analyte to be introduced directly into an analytical column of the supercritical fluid chromatograph. In one form of the present invention, the impactor is comprised of a porous ceramic frit which is formed in-situ at the end of a transfer tube in the transfer passage. The impactor-based interface serves to control the precipation of the analyte and the decompression of the supercritical fluid so as to minimize band broadening and provide sharp chromatograph peaks.

Additional advantages and features of the present invention will become apparent from a reading of the detailed description of the preferred embodiment which makes reference to the following set of drawings in which:

BRIEF DESCRIPTION OF THE DRAWINGS

FIG. 2 is a block diagram of the on-line multidimensional chromatographic system according to the present invention in the elution mode.

FIG. 3 is a block diagram of the on-line multidimensional chromatographic system according to the present invention in the sampling mode.

DETAILED DESCRIPTION OF THE PREFERRED EMBODIMENT

Figure 1:
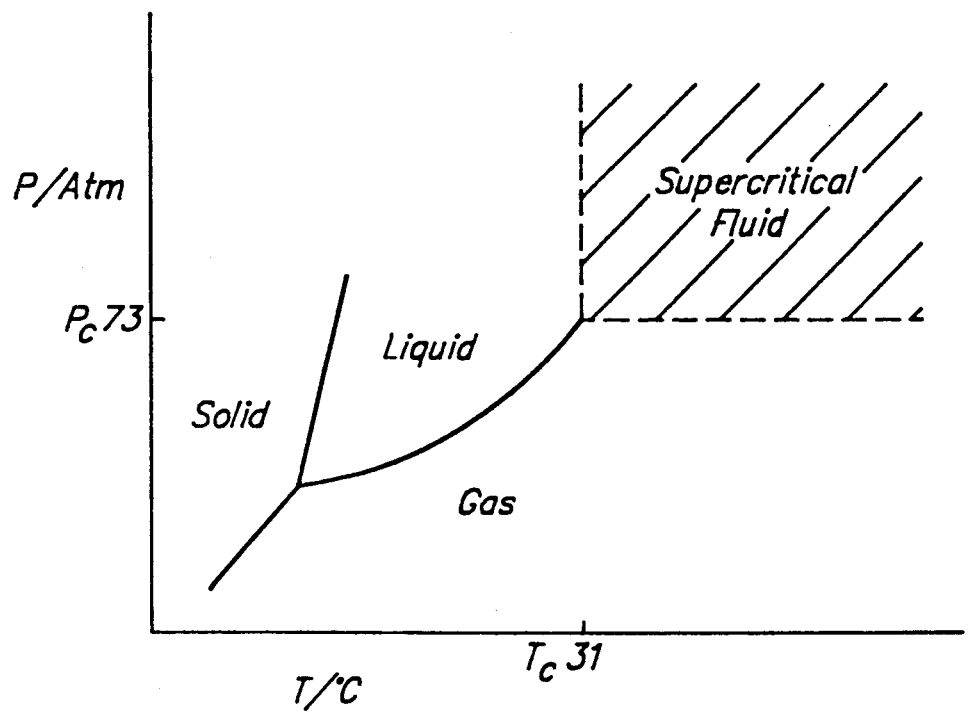
FIG. 1 is a phase diagram of carbon dioxide for illustrating the supercritical fluid range of one exemplary fluid capable of being utilized in the present invention.

Referring to FIG. 1, a phase diagram of carbon dioxide is shown to provide an exemplary illustration of a supercritical fluid. As shown in FIG. 1, the regions corresponding to the solid, liquid, and gaseous states are well defined. However, at temperatures exceeding the critical temperature ($T_c$), the densities of the liquid and vapor are identical and the fluid cannot be liquefied by increasing the pressure. The shaded area in the phase diagram illustrates the supercritical region. In this region, no phase change occurs, as the fluid is neither a liquid nor a gas. Rather, there is a transition from liquid to supercritical fluid as the temperature is increased at constant pressure, and there is also a transition from gas to supercritical fluid as the pressure is increased at constant temperature.

Carbon dioxide is particularly useful as a supercritical fluid, as it is relatively inexpensive, readily available, and has critical temperature and pressure properties which make it easy and practical to use in the supercritical region. However, one of the disadvantages of carbon dioxide is its lack of polarity at a molecular level. Accordingly, other fluids may be added to carbon dioxide, such as methanol, in order to provide a supercritical fluid mixture for extracting more polar materials or compounds in the appropriate application. As will be seen from the description below, a supercritical fluid stream is used to extract or recover analyte deposits from two different locations within the system according to the present invention. While carbon dioxide is a preferred supercritical fluid, it should be appreciated that other fluids (e.g., ammonia, acetonitrile, tetrahydrafuran) may be used alone or in combination with other fluids to provide a supercritical fluid which is suitable for extracting the analyte under investigation.

In general, extractions with supercritical fluids are faster and more efficient than conventional liquid or soxhelet extraction methods. Supercritical extraction is based upon the solubility of the analyte or target compound in the supercritical fluid, and this solubility property can be changed by varying the density of the particular supercritical fluid. In other words, a low density supercritical fluid approaching the qualities of a gas will typically not be as good an extraction fluid as one that approaches the densities of a liquid. Thus, the extraction strength of the supercritical fluid may be controlled by adjusting its density, which is in turn controlled by the temperature and pressure of the fluid. For example, because the compressibility of a supercritical is large above the critical temperature, small changes in the pressure applied to the fluid will result in large changes in the density of the fluid.

Supercritical fluid densities can be two to three orders of magnitude larger than those of a gas. As a result of this larger density, molecular interactions in supercritical fluids increase due to shorter intermolecular differences. On the other hand, the viscosity and mass transport properties of supercritical fluids remain similar to those of a gas. The gas-like/liquid-like quality of supercritical fluids allow similar solvent strengths as liquids along with improved mass transport. Since supercritical fluids offer these two properties simultaneously, they provide the potential for rapid extraction rates and more efficient extractions. Further discussion of supercritical fluid extraction may be found in "Supercritical Extraction Of Chlorpyrifos Methyl From Wheat At Part Per Billion Levels", by Robert M. Campbell, David W. Meunier and Hernan J. Cortes, in the Journal of Micro Column Separations, Volume 1, No. 6, 1989, Pages 302-308. This article is hereby incorporated by reference. An additional discussion of supercritical fluid extraction may be found in Cortes et al. U.S. patent application Ser. No. 594,106, entitled "On-Line Supercritical Fluid Extraction Multidimensional Chromatographic System", co-filed herewith. This commonly assigned patent application is hereby incorporated by reference.

Figure 4:
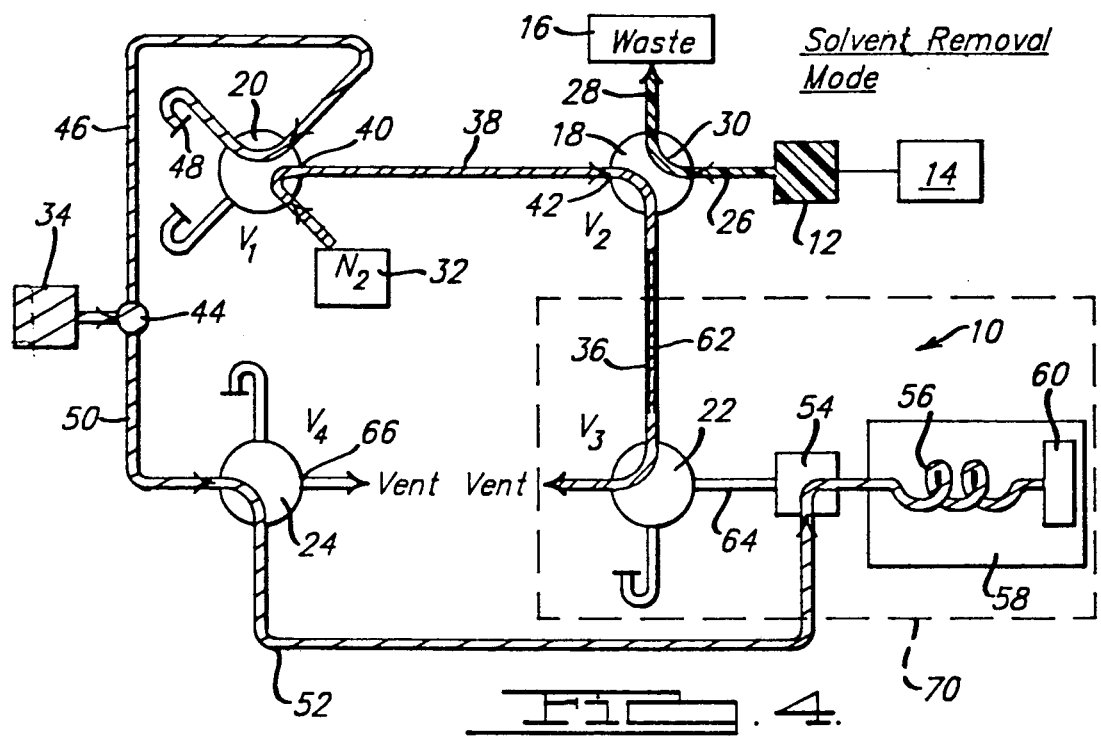
FIG. 4 is a block diagram of the on-line multidimensional chromatographic system according to the present invention in the solvent removal mode.
Figure 5:
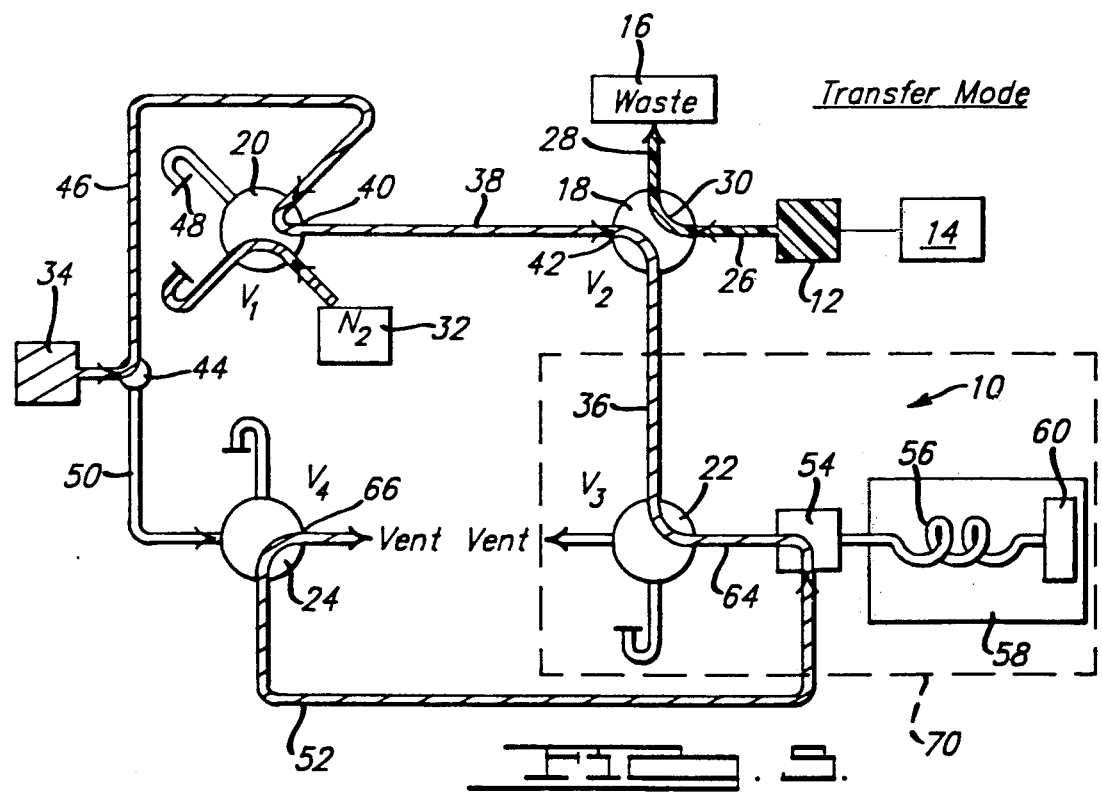
FIG. 5 is a block diagram of the on-line multidimensional chromatographic system according to the present invention in the transfer mode.

Referring to FIGS. 2-5, an on-line LC-SFC multidimensional chromatographic system 10 according to the present invention is shown in four different operating modes. In this regard, FIG. 2 illustrates the system 10 in an elution mode, FIG. 3 illustrates the system in a sampling mode, FIG. 4 illustrates the system in a solvent removal mode, and FIG. 5 illustrates the system in a transfer mode. Each of these four modes represent a different fluid flow configuration of system 10 for executing the method according to the present invention.

Referring specifically to FIG. 2, the system 10 is shown to include a liquid chromatograph 12 which receives a sample to be analyzed from an injector 14. In one form of the present invention, the liquid chromatograph 12 is a size exclusion chromatograph which employs a micro column for separating the sample material received from the injector 14 by molecular size. In this regard, the injector 14 introduces a predetermined volume of the sample material into a solvent stream of the liquid chromatograph 12. As an exemplary set of liquid chromatographic conditions, the micro column may be comprised of a 30 cm×250 μm fused silica column packed with PL-Gel mixed bed 10 μm packing. The solvent stream or eluent may be comprised of tetrahydrofuran ("THF") flowing at 3.0 μl/minute. The injector 14 may be comprised of a Valco Model NI4W injection valve from Valco Instruments, Houston, Tex., with an injection volume of 150 nL (500 nL rotor, time-split). The liquid chromatograph 12 also includes a detector, which may be a Jasco Uvidec V detector (at 254 nm, 6 nl cell) from Jasco International, Japan.

The liquid chromatograph detector is used to detect a particular section or fraction of interest eluting from the micro column of the liquid chromatograph in the solvent stream. In the elution mode of FIG. 2, the fluid flow eluting from the liquid chromatograph 12 is directed to a waste collector 16 until the fraction of interest is detected. In this regard, the system 10 includes a multi-port switching valve 18 for controlling the direction of fluid flow from the liquid chromatograph 12. In one form of the present invention, the valve 18 is a Valco ten port valve model NI10WT.

Valve 18 is one of four valves provided in system 10 for controlling fluid flow from three different sources, the fluid flow eluting from the liquid chromatograph being one of these sources. The other valves in the system 10 are identified as valves 20, 22 and 24. Each of these valves are multi-port switching valves, the number of ports for each valve being dependent upon the number of conduits and switching positions required for their operation in the system. Thus, for example, valves 18 and 20 may be identical ten-port Valco valves, while valves 22 and 24 may be four-port Valco valves (e.g., model AC4W).

While the valves 18-24 are shown to be separate valves, it should be appreciated that one or more of these valves may be combined into a single valve construction in the appropriate application. As will be apparent from the description below, several or all of the valves 18-24 should be switched simultaneously to change from one operating mode to another. While this switching action may be accomplished manually, it will be appreciated that the system 10 is capable of being fully automated, so that manual intervention is not necessary to change the valve positions.

In the elution mode, valve 18 directs the fluid eluting from the liquid chromatograph to the waste collector 16. This fluid communication is illustrated in FIG. 2 by the shading or hatching of the conduit sections 26-28 and the valve section 30. This procedure for illustrating fluid flow is utilized throughout FIGS. 2-5 in order clearly demonstrate the difference between the various modes of operation and the fluid communication provided in each of these modes. In this regard, a different form of shading or hatching is provided for each of the three fluid sources in system 10, namely the liquid chromatograph 12, a inert gas source 32 and a pump 34 for providing a supercritical fluid stream.

Continuing with the discussion of the elution mode, inert gas from gas source 32 is directed to flow through an inlet column 36 and out to a vent under the direction of valves 18, 20 and 22. This fluid flow circuit includes a conduit 38 which is used to connect port 40 of valve 20 to port 42 of valve 18. The purpose of this gas flow is to remove any fluid that may be present in the inlet column 36. The gas used to dry the inlet column 36 may be any suitable gas which is inert to the chemicals and materials used in the system. Thus, for example, the gas source 32 may be a gas cylinder supplying nitrogen to the system. In order to insure that any fluid present in the inlet column 36 is rapidly removed, it is preferred that the gas flow from source 32 be maintained at a relatively high gas pressure (e.g., 2-200 psi). Accordingly, it should be appreciated that the conduit 38 should be capable of withstanding and maintaining such pressures. Indeed, each of the conduits used to deliver fluid to components in the system, such as conduit 38, should be capable of withstanding and maintaining the pressures employed to convey the supercritical fluids used in the system (e.g., 1,000-10,000 psi). In one embodiment according to the present invention, each of these delivery conduits are preferably made of fused silica (250 μm i.d. × 400 μm o.d.). However, it should be understood that other suitable materials may be employed in the appropriate application.

The system 10 also includes a syringe pump 34 for producing the flow of a supercritical fluid, such as carbon dioxide. In one embodiment according to the present invention, the syringe pump is a Varian 8500 syringe pump from Varian Instruments, Sunnyvale, Calif. While this syringe pump permits manual control of the pressure (and hence the density) of the supercritical fluid, automated control may also be employ to control the pressure of the supercritical fluid. In this regard, the pressure provided by the pump 34 may be programmed ballistically to increase from a steady state delivery condition (e.g., 100 atmospheres) to an operative condition used for extraction (e.g., 400 atmospheres).

Supercritical fluid from pump 34 is split into two directions by a tee 44, which may be a stainless steel Model ZT1 from Valco Inc. The tee 44 is preferably equipped with stainless steel ferrule connectors to seal the tee. In one direction, the supercritical fluid is passed through a delivery conduit 46 to the valve 20, which blocks further flow by directing the flow to a plug 48. In the other direction, the supercritical fluid is passed through a delivery conduit 50 to the valve 24. Valve 24 is turn directs the supercritical fluid flow through a delivery conduit 52, which is connected to an interface 54. As will be more fully described in connection to FIG. 6, the interface 54 passes the supercritical fluid flow into an analytical column 56 of a supercritical flow chromatograph 58. This supercritical fluid flow circuit permits the pump to operate at its steady state pressure condition, so that there will be minimal delay when the pump is adjusted to increase the pressure to the operative pressure condition used for extraction purposes. This supercritical fluid flow circuit also serves to permit a detector 60 of the chromatograph 58 to produce a baseline output prior to its analysis of the sample injected into the liquid chromatograph 12.

Once the liquid chromatograph 12 detects the fraction of interest, the system 10 will enter the sampling mode. The fluid communication conditions for the sampling mode are shown in FIG. 3. In the sampling mode, the valve 18 will switch the fluid flow eluting from the liquid chromatograph into the inlet column 36, and the valve 18 will switch the gas flow from source 32 to the waste collector 16. Aside from this change of position for valve 18, the positions of the other valves 20-24 remain the same as they were in the elution mode. Thus, it should be appreciated that the fluid flow eluting from the liquid chromatograph 12 will travel through the inlet column 36 and out to a vent port of the valve 22.

The sampling mode is used to transfer the fraction of interest to the inlet column where at least a portion of this fraction will be deposited in the inlet column. In this regard, the inlet column is preferably an uncoated fused silica capillary (e.g., 5 m length, 250 micron i.d.), which will permit the target compound or analyte species from the fraction to spread along and be retained on the interior surface of the capillary as a temporary coating.

After the fraction of interest has been completely transferred to the inlet column 36, as determined by the liquid chromatograph detector and the solvent flow rate, the system 10 will enter the solvent removal mode. The fluid communication conditions for the solvent removal mode are shown in FIG. 4. As will be readily apparent from FIG. 4, the positions of the valve 18 is returned to the elution mode position, as shown in FIG. 2. However, FIG. 4 also illustrates the presence of the deposit on the interior surface of the inlet column 36 by reference number 62. In this regard, it should be understood that the illustration of the thickness of the deposit 62 has been greatly exaggerated so that it may be visually represented.

In the solvent removal mode, the high pressure gas flow from source 32 will rapidly remove substantially all of the liquid chromatograph solvent from the inlet column 36. However, the analyte or analytes of interest of deposit 62 will be retained in the inlet column 36 for subsequent transfer into the supercritical fluid chromatograph 58. In this way, the system 10 will permit a relatively large injection volume to be used for the liquid chromatograph separation step without requiring the introduction of the solvent into the supercritical fluid chromatograph 58.

After sufficient time has been permitted to remove the solvent from the inlet column 36 (e.g., 3-10 minutes), the system 10 is switched to the transfer mode shown in FIG. 5. In the transfer mode, the position of valve 20 is switched to permit supercritical fluid to flow through the inlet column 36 via conduits 46 and 38. This change of position for valve 20 also blocks gas flow from the gas source 32. The position of valve 22 is also changed to permit fluid flow from the inlet column 36 to enter the interface 54 via a restrictor conduit 64 of this interface.

The pressure provided by the pump 34 will also be increased in order to enable the supercritical fluid to extract the deposited analytes 62 from the inlet column 36 at a rapid rate. For example, this extraction process may take on the order of 5 minutes to complete. The supercritical fluid will carry the analytes of interest into the interface 54, where the analytes will be deposited or trapped in a confined area. This procedure is employed to concentrate the analyte or analytes prior to introduction into the analytical column 56 of the supercritical fluid chromatograph, so that the chromatogram peaks produced by the detector 60 will be sharp.

The interface 54 traps the analytes by permitting the supercritical fluid to decompress into a gas and be vented from the interface via conduit 52. In this regard, valve 24 is positioned in the transfer mode to couple conduit 52 to a vent port 66.

After the analytes have been deposited in the interface 54, the system 10 is then switched back to the elution mode shown in FIG. 2. This subsequent elution mode may be referred to as an analytical mode, as the supercritical fluid flow into the interface 54 from conduit 52 will cause the trapped analytes to be introduced into the analytical column 56 of the chromatograph 58. In other words, the supercritical fluid will wash the analytes from the interface 54 and convey them to the analytical column 56, where another separation and detection step will begin. Specifically, the analytical column 56 will separate one or more constituents of interest from the analytes, and these constituents will be detected and quantified by the detector 60 of the chromatograph 58.

In order to illustrate one set of exemplary chromatographic conditions, the analytical column 56 may be comprised of a 3.0 m $\times$ 50 $\mu$m column with a 0.25 $\mu$m Phenyl-methyl silicone film from Dionex/Lee Scientific, Salt Lake City, Utah. Similarly, the detector 60 may be comprised of a flame ionization detector (set at 370° C.), from Hewlett Packard, Inc., Belafonte, Pa. With carbon dioxide as the supercritical fluid, the pressure produced by pump 34 should be increased from 100 atm. to 400 atm. at a rate of 15 atm./min.

In order to control the temperature of the supercritical fluid extraction process and the analytical process, an oven 70 is preferably provided to enclose the inlet column 36, the valve 22 and the chromatograph 58. In this regard, the temperature is set to maintain the carbon dioxide in a supercritical fluid state (e.g., 100° C.) in combination with the pressure produced by the pump 34. This temperature condition also serves to aid in the process of removing solvent from the inlet column 36 in the solvent removal mode, as the solvent will tend to vaporize at an increased temperature.

Figure 6:
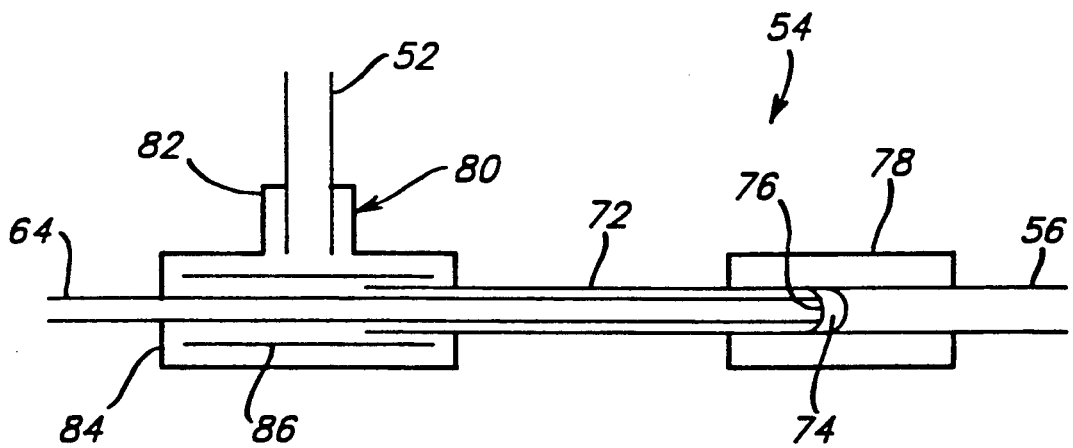
FIG. 6 is a diagrammatic representation of the restrictor interface shown in FIGS. 2-5.

Referring to FIG. 6, the interface 54 is shown to include the restrictor tube 64 which is coaxially disposed in a transfer tube 72. Both the restrictor tube 64 and the transfer tube 72 are preferably fused silica capillaries from Polymicro Technologies, Inc. In the case of the restrictor tube 64, the inner diameter is preferably in the range between 10 $\mu$m and 25 $\mu$m in order to cause the supercritical fluid to decompress slowly while the outer diameter is closely related to the inner diameter of the transfer tube 72. For example, with an outer diameter of 250 $\mu$m for the restrictor tube 64, the inner diameter of the transfer tube should be approximately 300-400 $\mu$m. Similarly, for a restrictor tube having an inner diameter of 15 $\mu$m and an outer diameter of 150 $\mu$m, the inner diameter of the transfer tube should be 160-200 $\mu$m with an outer diameter of 350 $\mu$m. In other words, the inner diameter of the transfer tube 72 should be just enough larger than the outer diameter of the restrictor tube 64 to permit the restrictor tube to slide into and be held by the transfer tube 72 without otherwise providing support between the restrictor tube and the transfer tube. As for the length of the restrictor and transfer tube sections, the transfer tube 72 need only be long enough to permit the connections at each end to be made (e.g., 3 cm). In contrast, the length of the linear restrictor tube 64 should be long enough to assist in controlling the decompression of the supercritical fluid (e.g., 15-20 cm).

As shown in FIG. 6, the restrictor interface 54 also includes an impactor 74 for trapping the target compound or analyte as the supercritical fluid decompresses into a gas and escapes back through the transfer tube 72. In this regard, the impactor 74 is used to dissipate any kinetic energy that may be present during the decompression of the supercritical fluid, and provide a surface upon which the target compound may be deposited or precipitated. Specifically, the impactor 74 should be constructed to minimize excessive travel or spreading of the target compound, so that narrow/sharp chromatographic bands may be produced by the chromatograph 58. In one form of the present invention, the impactor 74 is a porous ceramic frit formed in situ at the end of the transfer tube 72 according to U.S. Pat. No. 4,793,920. As discussed more fully in this patent, the end of the transfer tube 72 is dipped into liquid potassium silicate with a catalyst, and capillary action is allowed to bring the liquid into the tube (e.g., 0.1-1.0 mm). The tube is then heated to polymerize the material to create the frit with a porosity on the order of 5,000 angstroms, and it is cut to a desired length. The impactor 74 may subsequently be deactivated if desired. While the impactor 74 could be comprised of a solid block of material (e.g., quartz) disposed at or press fitted into the end of the transfer tube 72 (leaving gaps for fluid flow), such a construction is not considered to be as effective as a cast in-situ porous ceramic frit in terms of concentrating the precipitation of the target compound in a limited area.

The end of the restrictor tube 64 is preferably disposed very close to the impactor 74 so that there is a minimum distance between the restrictor tube 64 and the impactor 74. In this way, the target compound will be deposited generally on the forward surface 76 of the impactor 74. As shown in FIG. 6, the end of the transfer tube 72 is joined to the end of the analytical column 56 in a butt connection via glass lined stainless steel union 78. Thus, the union 78 is disposed at the junction between the restrictor tube 64, the transfer tube 72 and the analytical column 56, with the impactor 74 being interposed between each of these tubes at this junction. It should also be appreciated that this construction advantageously minimizes the distance between the point of decompression and the analytical column 56. In one form of the present invention, the union 78 is a model VSU/004 union from Scientific Glass Engineering, Austin, Tex.

FIG. 6 also shows that the opposite end of the transfer tube 72 is contained in a 3-way glass-lined stainless steel tee 80. The transfer conduit 52 is connected to the lateral or vertically extending leg 82 of the tee 80 to permit the decompressed supercritical fluid (i.e., gaseous carbon dioxide) to escape from the restrictor interface and be vented from the system. The tee 80 also supports the restrictor tube 64 at leg 84 in coaxial alignment with the transfer tube 72. In one form of the present invention, the tee 80 is a model YSUT004 tee from Scientific Glass Engineering. This particular tee is equipped with graphite-vespel ferules and connectors for providing a seal between the tee 80 and the tubes. A deactivated fused silica sleeve 86 (e.g. 3.5 cm × 200 $\mu$m when the transfer tube outer diameter is 150 $\mu$m) may also be coaxially disposed in the tee 60 to minimize any dead space in the tee.

Additionally, it may be desireable in the appropriate application to provide a method of cooling the restrictor interface (e.g. by passage of liquid nitrogen or carbon dioxide) to assist the trapping of the target compound and minimize any broadening of the chromatogram peaks. In this regard, it should be noted that the transition from supercritical fluid to gas will create a cooling effect (Juoule-Thompson), which should aid in keeping the analytes in a narrow band. In any event, the need for additional cooling is substantially minimized by the use of a porous ceramic frit for the impactor due to its large surface area.

While the impactor 74 is formed in the transfer tube 72, it may also be possible to form the impactor at the front of the analytical column 56. With such a construction, the transfer tube 72 may not be necessary. Similarly, it should be appreciated that a single housing may be constructed to replace the separate components used for the tee 80 and the union 78.

It will be appreciated that the above disclosed embodiment is well calculated to achieve the aforementioned objectives of the present invention. In addition, it is evident that those skilled in the art, once given the benefit of the foregoing disclosure, may now make modifications of the specific embodiment described herein without departing from the spirit of the present invention. Such modifications are to be considered within the scope of the present invention which is limited solely by the scope of the spirit of the appended claims.

What is claimed is:

1. A method of providing on-line SFC chromatographic analysis of a sample in a large solvent volume, comprising the steps of:
    depositing at least a portion of a sample from a solvent fluid stream of a liquid chromatograph into an inlet column;
    removing at least a portion of said solvent from said inlet column;
    causing a supercritical fluid to flow through said inlet column to extract an analyte from said deposited sample, and trapping said analyte in an interface while decompressing and venting said supercritical fluid from said interface; and
    introducing said trapped analyte into a supercritical fluid chromatograph to separate and analyze a constituent of interest of said analyte.

2. The method according to claim 1, wherein said trapped analyte is introduced into said supercritical fluid chromatograph by causing said supercritical fluid to flow through said interface.

3. The method according to claim 1, wherein said interface includes impactor means for trapping said analyte on a surface disposed in proximity to the decompression of said supercritical fluid.

4. The method according to claim 1, wherein said inlet means is an uncoated and deactivated fused silica column.

5. A method of providing on-line LC-SFC multidimensional chromatographic analysis, comprising the steps of:
    introducing a sample material into a solvent stream of a liquid chromatograph to separate and detect a fraction of interest from said sample by liquid chromatography;
    directing the fluid flow eluting from said liquid chromatograph into an inlet column when said fraction of interest is detected, and depositing at least a portion of said fraction of interest in said inlet column;
    directing a gas stream into said inlet column after said depositing step to remove at least a portion of elution fluid from said inlet column;
    directing a supercritical fluid stream into said inlet column after said gas stream removal step to extract an analyte from said deposit, and trapping said analyte in an interface while decompressing and venting said supercritical fluid from said interface; and
    introducing said trapped analyte into a supercritical fluid chromatograph to separate and analyze a constituent of interest from said analyte by directing said supercritical fluid stream through said interface.

6. The method according to claim 5, wherein said interface includes impactor means for trapping said analyte on a surface disposed in proximity to the decompression of said supercritical fluid.

7. The method according to claim 6, wherein said inlet means is a uncoated and deactivated fused silica column.

* * * * *